(12) United States Patent
Sase

(10) Patent No.: US 12,409,344 B2
(45) Date of Patent: Sep. 9, 2025

(54) PROBE FOR ULTRASONIC TREATMENT TOOL, METHOD FOR PRODUCING SAME, AND ULTRASONIC TREATMENT TOOL

(71) Applicant: OLYMPUS CORPORATION, Tokyo (JP)

(72) Inventor: Ryuichi Sase, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 150 days.

(21) Appl. No.: 18/217,588

(22) Filed: Jul. 2, 2023

(65) Prior Publication Data

US 2023/0347183 A1    Nov. 2, 2023

Related U.S. Application Data

(63) Continuation of application No. PCT/JP2021/017525, filed on May 7, 2021.

(51) Int. Cl.
| | |
|---|---|
| *A61N 7/00* | (2006.01) |
| *C21D 1/18* | (2006.01) |
| *C21D 6/00* | (2006.01) |
| *C21D 9/00* | (2006.01) |
| *C22C 38/00* | (2006.01) |
| *C22C 38/02* | (2006.01) |
| *C22C 38/04* | (2006.01) |
| *C22C 38/40* | (2006.01) |

(52) U.S. Cl.
CPC ................. *A61N 7/00* (2013.01); *C21D 1/18* (2013.01); *C21D 6/004* (2013.01); *C21D 6/005* (2013.01); *C21D 6/008* (2013.01); *C21D 9/00* (2013.01); *C22C 38/002* (2013.01); *C22C 38/02* (2013.01); *C22C 38/04* (2013.01); *C22C 38/40* (2013.01); *C21D 2211/00* (2013.01)

(58) Field of Classification Search
CPC . A61N 7/00; C21D 1/18; C21D 6/005; C21D 6/004; C21D 6/008; C21D 9/00
See application file for complete search history.

(56) References Cited

U.S. PATENT DOCUMENTS

| | | | |
|---|---|---|---|
| 5,167,725 A | 12/1992 | Clark et al. | |
| 5,760,529 A | * 6/1998 | Tamai | H02N 2/106 |
| | | | 310/323.15 |

(Continued)

FOREIGN PATENT DOCUMENTS

| | | |
|---|---|---|
| CN | 105886706 A | 8/2016 |
| JP | H01-309944 A | 12/1989 |

(Continued)

OTHER PUBLICATIONS

Hirone, Tokutaro et al., Attenuation of Ultrasonic Waves in Metals (III). Attenuation in Chromium-Molydenum Steels. Journal of the Japan Institute of Metals. 1954, vol. 18, No. 3, pp. 185-188.

(Continued)

*Primary Examiner* — Gerald Johnson
(74) *Attorney, Agent, or Firm* — Scully, Scott, Murphy & Presser, P.C.

(57) ABSTRACT

A probe for an ultrasonic treatment tool is configured to transmit ultrasonic vibration to a biological tissue. The probe includes a substrate including a stainless steel, a structure of the stainless steel including one or both of troostite and sorbate.

7 Claims, 7 Drawing Sheets

(56) References Cited

U.S. PATENT DOCUMENTS

| | | | |
|---|---|---|---|
| 2010/0191173 A1* | 7/2010 | Kimura | A61M 3/0258 |
| | | | 606/41 |
| 2013/0031980 A1* | 2/2013 | Sako | B06B 1/0292 |
| | | | 156/60 |
| 2017/0347914 A1* | 12/2017 | Isaacson | A61B 8/0841 |
| 2019/0142450 A1 | 5/2019 | Shimamura et al. | |
| 2021/0121831 A1* | 4/2021 | Aljundi | B01D 69/148 |
| 2023/0151509 A1* | 5/2023 | Waidelich | A61B 17/00 |
| | | | 428/336 |

FOREIGN PATENT DOCUMENTS

| | | |
|---|---|---|
| JP | 2008-289876 A | 12/2008 |
| JP | 6055996 B2 | 1/2017 |
| JP | 2018-514355 A | 6/2018 |
| WO | 2016/170520 A1 | 10/2016 |
| WO | 2018/011896 A1 | 1/2018 |

OTHER PUBLICATIONS

International Search Report dated Jun. 8, 2021 received in PCT/JP2021/017525.

* cited by examiner

PROBE FOR ULTRASONIC TREATMENT TOOL, METHOD FOR PRODUCING SAME, AND ULTRASONIC TREATMENT TOOL

CROSS-REFERENCE TO RELATED APPLICATIONS

The present application is a continuation application based on PCT Patent Application No. PCT/JP2021/017525, filed on May 7, 2021, the entire content of which is hereby incorporated by reference.

BACKGROUND

Technical Field

Embodiments of the present invention relate to a probe for an ultrasonic treatment tool, a method for producing the same, and an ultrasonic treatment tool.

Description of the Background

An ultrasonic treatment tool includes an ultrasonic transducer and a probe that transmits ultrasonic vibration of the ultrasonic transducer to a biological tissue that is an object to be treated.

By resonating with the ultrasonic vibration from the ultrasonic transducer, the probe can efficiently transmit to the object ultrasonic vibration capable of treating the object.

For example, Japanese Unexamined Patent Application, First Publication No. 2008-289876 (hereinafter referred to as Patent Document 1) describes a probe which is formed by materials such as titanium alloy, duralumin, and stainless steel and in which the resonance frequency can be adjusted.

For example, Japanese Patent Publication No. 6055996 (hereinafter referred to as Patent Document 2) describes detecting temperature changes in an ultrasonic probe and controlling the oscillation frequency of an ultrasonic transducer.

Various elements are added to titanium alloy used for the probe to improve its strength. For example, α+β type titanium alloy including expensive vanadium is known as a titanium alloy used as a material of the probe. The probe using titanium alloy is expensive and is not suitable for a single-use ultrasonic treatment tool.

As described in Patent Document 1, for example, the probe may be made of a metal material such as stainless steel, which is cheaper than titanium alloy, but stainless steel generates a large amount of heat during ultrasonic vibration. When the probe is used for a certain amount of time, the natural frequency of the probe changes due to temperature changes, so that it no longer resonates at the oscillation frequency of the ultrasonic transducer. In this case, the operation may not be continued.

For example, as in the technology disclosed in Patent Document 2, temperature changes in the probe may be detected to control the oscillation frequency of the ultrasonic transducer. In this case, the device becomes expensive because a temperature sensor and a control circuit are required.

SUMMARY

The present invention provides a probe for an ultrasonic treatment tool, a method for producing the same, and an ultrasonic treatment tool, which can suppress heat generation when stainless steel is included in the material of the probe and can be used for a long time without temperature control.

A first aspect of the present invention is a probe for an ultrasonic treatment tool, the probe being configured to transmit ultrasonic vibration to a biological tissue, the probe including: a substrate including a stainless steel, a structure of the stainless steel including one or both of troostite and sorbate.

A second aspect of the present invention is a method for producing a probe for an ultrasonic treatment tool, the method including: a first step of forming a substrate having a shape of the probe from a stainless steel material; a second step of holding the substrate at a temperature of 1010° C. or higher and 1070° C. or lower and quenching at a cooling rate equal to or higher than a critical cooling rate; and a third step of tempering the substrate at a temperature of 350° C. or higher and 700° C. or lower.

A third aspect of the present invention is an ultrasonic treatment tool including the probe according to the first aspect.

According to the probe for an ultrasonic treatment tool of the first aspect, the method of producing the probe for an ultrasonic treatment tool of the second aspect, and the ultrasonic treatment tool of the third aspect, when stainless steel is included in the material of the probe, heat generation can be suppressed and the probe can be used for a long time without temperature control.

DETAILED DESCRIPTION

Embodiments

A probe for an ultrasonic treatment tool, a method for producing the same, and an ultrasonic treatment tool according to an embodiment of the present invention will be described below with reference to the accompanying drawings.

Figure 1:
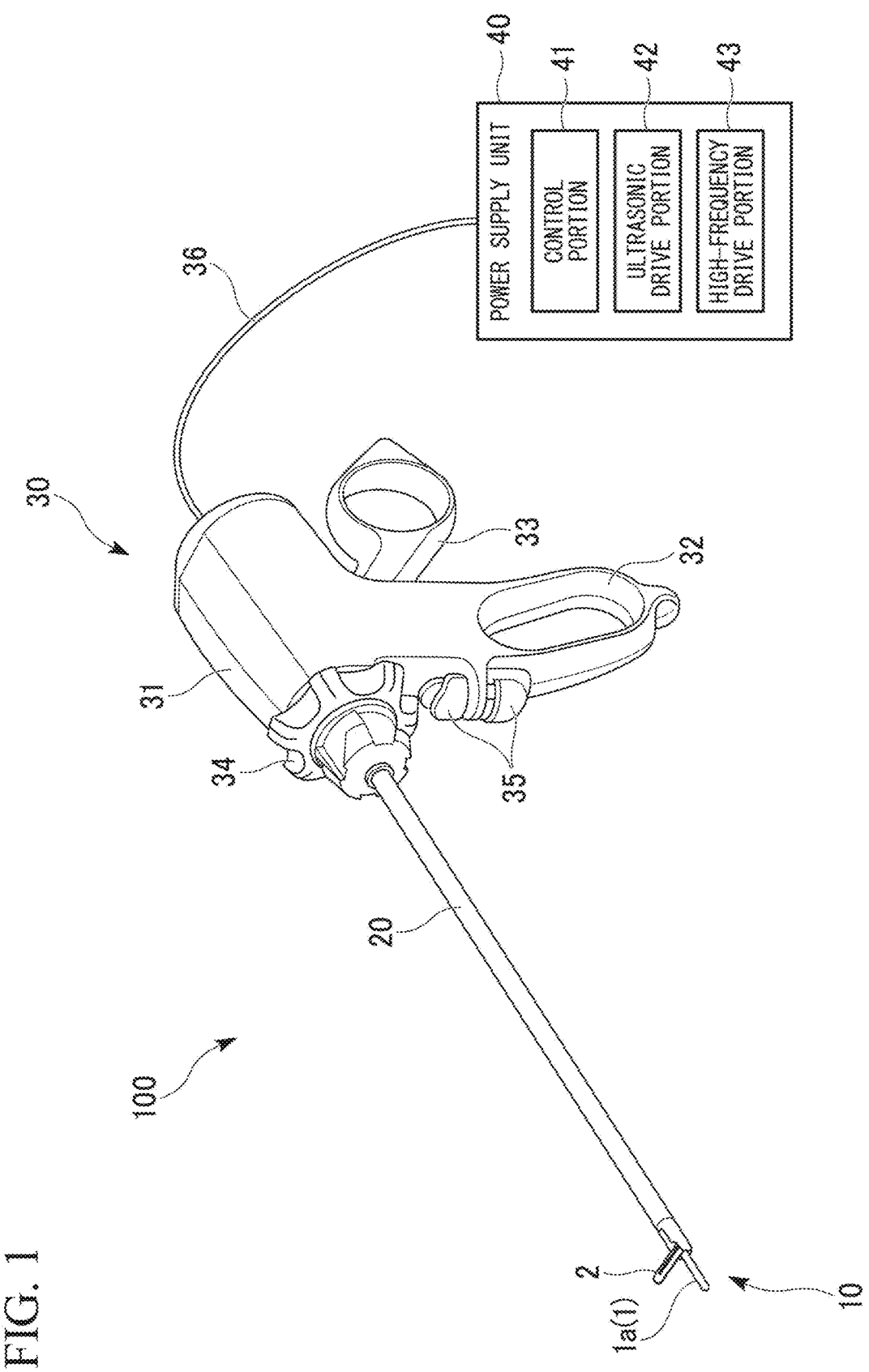
FIG. 1 is a schematic perspective view showing an example of an ultrasonic treatment tool according to an embodiment of the present invention.
Figure 2:
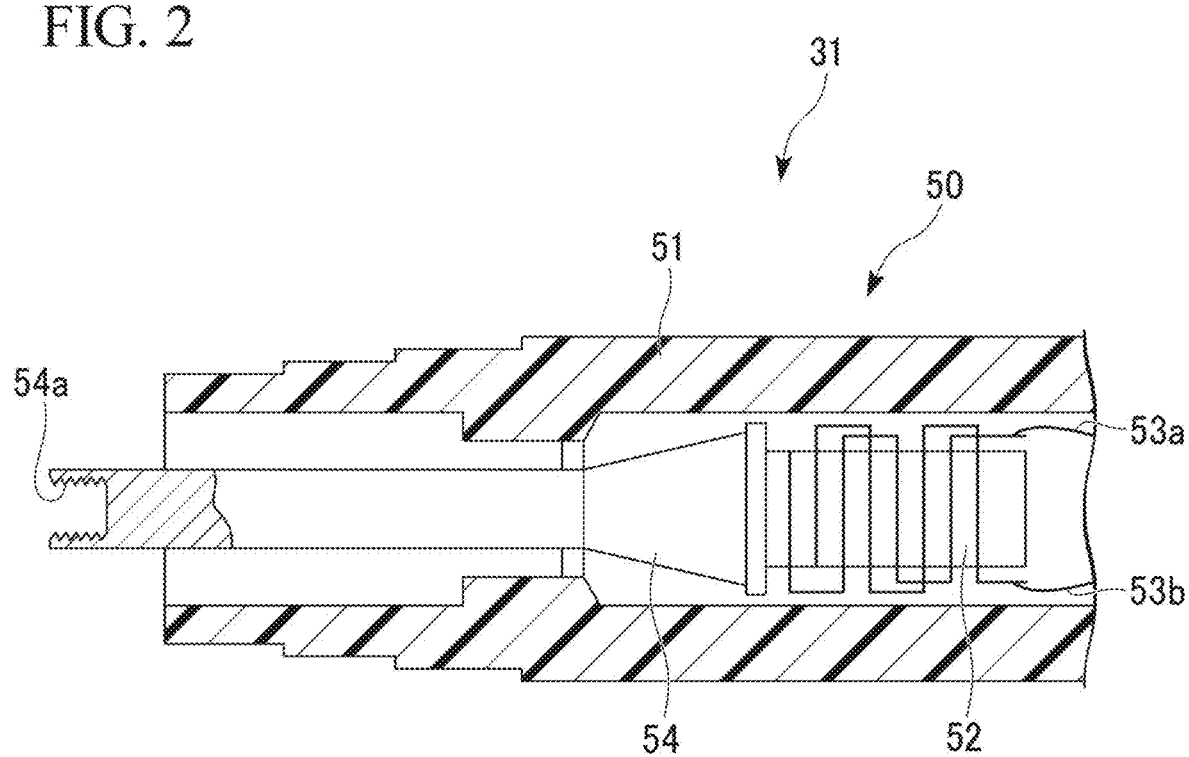
FIG. 2 is a schematic cross-sectional view showing an example of a transducer unit in an ultrasonic treatment tool according to the embodiment of the present invention.

FIG. 1 is a schematic perspective view showing an example of an ultrasonic treatment tool according to an embodiment of the present invention. FIG. 2 is a schematic cross-sectional view showing an example of the transducer unit in the ultrasonic treatment tool according to the embodiment of the invention.

As shown in FIG. 1, an ultrasonic treatment tool 100 according to this embodiment includes a treatment portion 10, a shaft 20, an operation portion 30, and a power supply unit 40.

The treatment portion 10, the shaft 20, and the operation portion 30 are arranged in this order along the longitudinal direction of the shaft 20. The treatment portion 10 constitutes the distal end portion of the ultrasonic treatment tool 100. The operation portion 30 constitutes the proximal end of the ultrasonic treatment tool 100.

The treatment portion 10 grips a biological tissue (for example, a blood vessel) to be treated, and applies high-frequency voltage to the gripped biological tissue to seal or coagulate the biological tissue. Furthermore, the treatment portion 10 cuts the grasped biological tissue while sealing it using ultrasonic vibration.

The treatment portion 10 includes a probe treatment portion 1a and a jaw 2.

The probe treatment portion 1a is provided at the distal end of a probe 1 (substrate).

The probe 1 is a rod-shaped member that is inserted through the shaft 20 and extends to the operating portion 30. Ultrasonic vibration is applied to the proximal end of the probe 1. As a result, the probe 1 is ultrasonically vibrated in the longitudinal direction, and the ultrasonic vibration is transmitted to the biological tissue that contacts with the probe treatment portion 1a.

A high-frequency voltage can also be applied to the probe 1 in this embodiment.

The detailed configuration of the probe 1 will be described later.

The jaw 2 is provided so as to be capable of opening and closing with respect to the probe treatment portion 1a. By opening and closing the jaw 2 with respect to the probe treatment portion 1a, the probe treatment portion 1a and the jaw 2 grip the biological tissue.

A part of the probe treatment portion 1a and a part of the jaw 2 function as bipolar electrodes that apply a high-frequency voltage to the gripped biological tissue. However, part of the probe treatment portion 1a and part of the jaw 2 may function as monopolar electrodes.

The shaft 20 includes a hollow sheath. The probe 1 is arranged inside the sheath of the shaft 20.

The jaw 2 is fixed to the distal end of the shaft 20 so that it can be opened and closed.

The probe treatment portion 1a of the probe 1 extends from the distal end of the shaft 20 toward the distal end.

The operation portion 30 is provided with an operation portion main body 31, a fixed handle 32, a movable handle 33, a rotation knob 34, and an output switch 35.

As shown in FIG. 2, an ultrasonic transducer unit 50 is provided inside the operation portion main body 31.

The ultrasonic transducer unit 50 includes a transducer case 51. Inside the transducer case 51, an ultrasonic transducer 52 that generates ultrasonic vibration by an inverse piezoelectric effect is provided.

Electric signal lines 53a and 53b are connected to the ultrasonic transducer 52.

The electrical signal lines 53a and 53b are electrically connected to the power supply unit 40. A driving signal for ultrasonically vibrating the ultrasonic transducer 52 is supplied from the power supply unit 40 to the electric signal lines 53a and 53b.

A columnar horn 54 is connected to the distal end of the ultrasonic transducer 52 in order to increase the amplitude of the ultrasonic vibration. The horn 54 is supported by the transducer case 51. A female threaded portion 54a is formed at the distal end of the horn 54.

As shown in FIG. 1, the fixed handle 32 is fixed to the operation portion main body 31.

The movable handle 33 is displaced with respect to the operation portion main body 31. The movable handle 33 is connected to a wire or rod inserted through the shaft 20 and connected to the jaw 2 inside the operation portion main body 31. Displacement of the movable handle 33 based on manipulation by the operator is transmitted to the jaw 2 through a wire or rod to which the movable handle 33 is connected. Thereby, the jaw 2 is displaced with respect to the probe treatment portion 1a in accordance with the movement of the movable handle 33.

The rotation knob 34 is provided for rotating the shaft 20 and the treatment portion 10. The rotation knob 34 is attached to the distal end portion of the operation portion main body 31 so as to be rotatable around the central axis of the shaft 20. When the operator rotates the rotation knob 34, the treatment portion 10 and the shaft 20 rotate according to the amount of rotation. Thereby, the angle of the treatment portion 10 around the shaft 20 with respect to the operation portion 30 is adjusted.

The output switch 35 includes, for example, two buttons. When one of the buttons is pressed, the output switch 35 outputs a signal for applying a high-frequency voltage and driving the ultrasonic transducer by the treatment portion 10. As a result, the biological tissue gripped by the treatment portion 10 is sealed or coagulated and cut. Further, when the other button is pressed, the output switch 35 outputs a signal that causes the treatment portion 10 to apply only the high-frequency voltage and not to drive the ultrasonic transducer. As a result, the biological tissue gripped by the treatment portion 10 is sealed or coagulated without being cut.

One end of a cable 36 is connected to the proximal end side of the operation portion 30. The other end of the cable 36 is connected to the power supply unit 40.

Inside the cable 36, electrical signal lines 53a and 53b and electrical signal lines for applying high-frequency power to the probe treatment portion 1a and the jaw 2 are inserted.

The power supply unit 40 includes a control portion 41, an ultrasonic drive portion 42 and a high-frequency drive portion 43.

The control portion 41 controls each portion of the ultrasonic treatment tool 100. For example, the control portion 41 controls the operation of the ultrasonic drive portion 42 and the high-frequency drive portion 43 according to the operation input from the output switch 35.

The ultrasonic drive portion 42 drives the ultrasonic transducer 52 (see FIG. 2) according to the control signal transferred from the control portion 41. A drive signal from the ultrasonic drive portion 42 is applied to the ultrasonic transducer 52 through the electrical signal lines 53a and 53b (see FIG. 2) inserted through the cable 36.

The high-frequency drive portion 43 supplies high-frequency current to the treatment portion 10 according to the control signal transferred from the control portion 41. High-frequency power is applied to the probe treatment portion 1a and the jaw 2, which constitute bipolar electrodes, through an electric signal line (not show-n) inserted through the cable 36.

The detailed shape of the probe 1 will be described.

Figure 3:
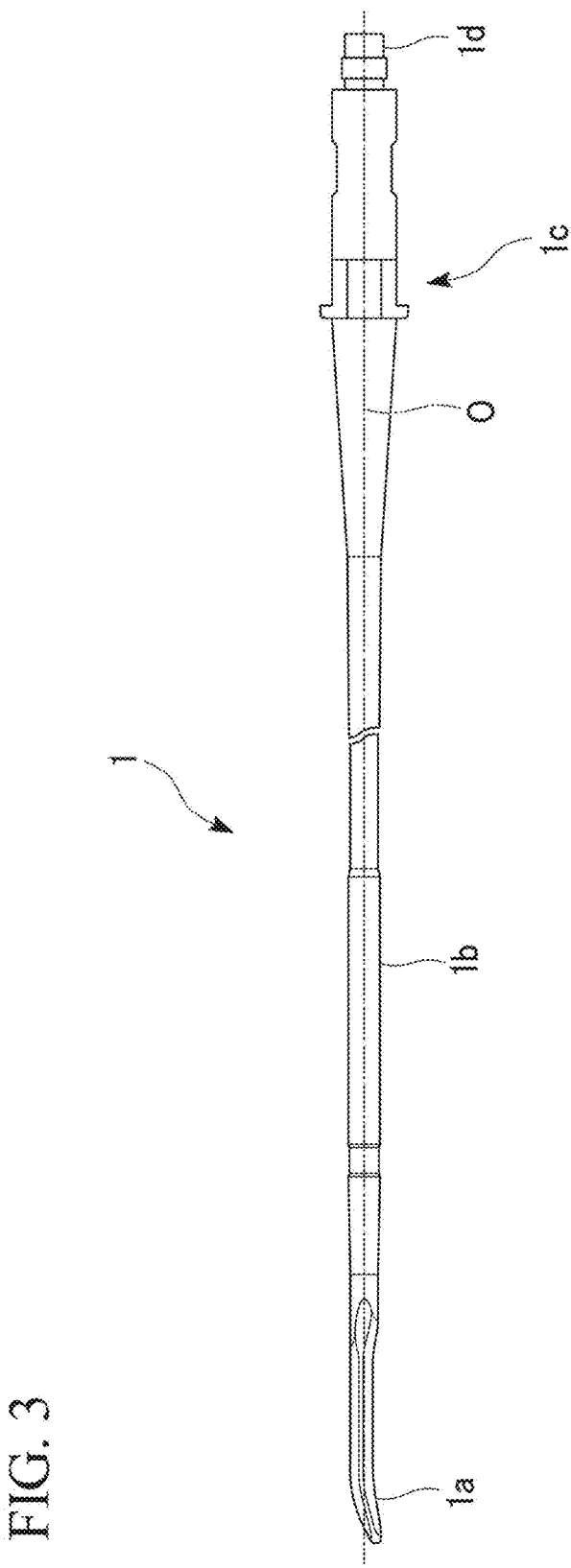
FIG. 3 is a schematic front view showing a probe for the ultrasonic treatment tool according to the embodiment of the present invention.

FIG. 3 is a schematic front view showing the probe for the ultrasonic treatment tool according to the embodiment of the present invention.

As shown in FIG. 3, the outer shape of the probe 1 as a whole is rod-shaped along the linear axis O. The profile of the probe 1 is partially changed in the longitudinal direction.

For example, the probe treatment portion 1a is slightly curved in a direction intersecting the axis O so that the biological tissue can be sandwiched between the probe treatment portion 1a and the jaw 2, at a position where the jaw 2 is closed.

A columnar portion 1b having a substantially constant outer diameter extends around the axis O on the proximal end side of the probe treatment portion 1a.

A proximal end portion 1c formed in an appropriate shape and fixed to the operation portion main body 31 extends from the proximal end side of the columnar portion 1b.

At the proximal end of the proximal end portion 1c, a male threaded portion 1d that is screwed into the female threaded portion 54a of the horn 54 (see FIG. 2) is provided.

When the male threaded portion 1d is screwed into the female threaded portion 54a and connected to the horn 54, the ultrasonic vibration generated by the ultrasonic transducer 52 is transmitted to the probe treatment portion 1a via the horn 54.

The probe 1 includes a substrate including a stainless steel including one or both of troostite and sorbite as a structure. For example, the probe 1 may be formed of a combination of a substrate and other members, but it is more preferable that the part that resonates with the applied ultrasonic vibration be formed of the substrate.

In the example shown in FIG. 3, the probe 1 is made of only the substrate.

The type of stainless steel used for the probe 1 is not particularly limited as long as one or both of troostite and sorbite are formed.

Troostite is a mixed structure of ferrite and fine carbide particles, and is a structure formed when martensite is tempered at a temperature of about 400° C.

Sorbite is a structure that occurs when martensite is tempered at a temperature of about 500° C. to about 650° C. Like troostite, sorbite is a mixed structure of ferrite and fine carbide particles. However, the particle size of the carbide particles in sorbite is larger than that in troostite, and the distance between the particles also increases in sorbite. For this reason, troostite has a finer and denser structure than sorbite.

For example, when stainless steel is held at a temperature of 1010° C. or higher and 1070° C. or lower and then quenched at a cooling rate equal to or higher than the critical cooling rate, martensite is obtained. After that, the stainless steel is tempered at a temperature of, for example, 350° C. or more and 700° C. or less to obtain a structure including one or both of troostite and sorbite.

In particular, tempering at a temperature of 350° C. or higher and 450° C. or lower increases the ratio of troostite, so that the average value of the distance between carbide particles becomes 0.5 µm or less.

Troostite and sorbite included in stainless steel can be distinguished by microscopic observation of the structure at high magnification.

For example, when the steel structure includes carbide particles and the carbide particles can be clearly observed using an optical microscope, it is sorbite, and when the carbide particles cannot be clearly observed without an electron microscope, it is trostite. Since the resolution of an optical microscope is about 0.2 µm, when there are many carbide particles of 0.2 µm or less, it can be said to be troostite. However, when carbide particles with various particle sizes are mixed, it is in a state of including both troostite and sorbite, and it may not be possible to clearly distinguish between the individual compartments.

Since sorbite is a structure in which the precipitation of carbide particles has progressed, it is observed that many carbide particles exist independently of ferrite. On the other hand, since troostite has a structure including carbide particles in the process of precipitation, it is observed that some carbide particles and ferrite are present in combination.

In troostite and sorbite, the carbide particles have a particle size and particle shape specific to high-temperature tempering, and a person skilled in the art can clearly distinguish them from, for example, a steel structure without carbide particles, ferrite containing cementite, bainite, and the like.

Below, one or both of troostite and sorbite are referred to as "high-temperature tempered structure".

Figure 4:
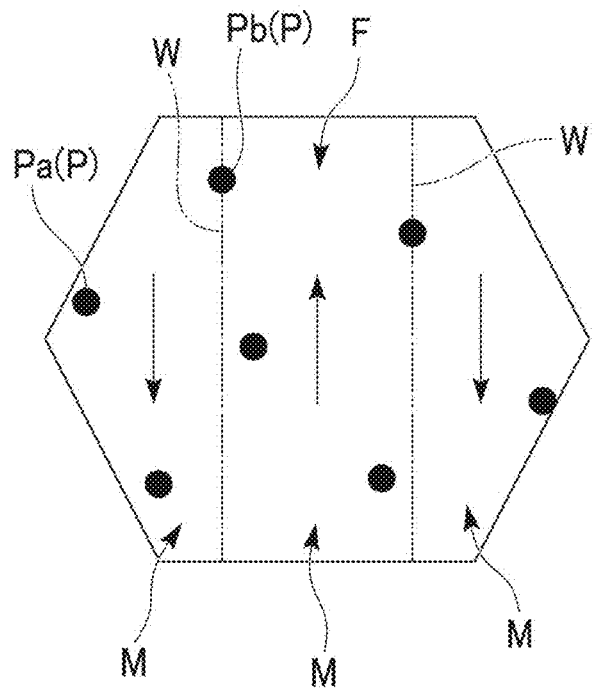
FIG. 4 is a schematic diagram showing an example of a structure of a substrate in the probe for the ultrasonic treatment tool according to the embodiment of the present invention.

FIG. 4 is a schematic diagram showing an example of the structure of the substrate in the probe for an ultrasonic treatment tool according to the embodiment of the present invention.

In the cross section of the inside of the crystal particles schematically shown in FIG. 4, ferrite F and carbide particles P are mixed in stainless steel having a high-temperature tempered structure.

Phyllite F is divided into a plurality of magnetic domains M. Each magnetic domain M differs from other adjacent magnetic domains M in the direction of the magnetic moment schematically indicated by an arrow, and between the magnetic domains M adjacent to each other, a domain wall W is formed in which the direction of the magnetic moment changes.

However, since FIG. 4 is a schematic diagram, it does not accurately represent the number and size of the magnetic domains M and the number and size of the carbide particles P.

It is more preferable that the particle size of the crystal particles in the stainless steel not be too large in terms of making it easier to suppress heat generation. For example, the particle size of the crystal particles is more preferably 1 µm or more and 10 µm or less.

The carbide particles P are formed according to the carbon content in the stainless steel. The carbide particles P have particle diameters according to precipitation conditions such as tempering temperature, and are distributed apart from each other inside the metal crystal.

Because the carbide particles P are randomly precipitated regardless of the magnetic properties of the ferrite F, some of the carbide particles P precipitate on the domain wall W when the number of particles increases to some extent. For example, in FIG. 4, the carbide particles Pa are the carbide particles P within the magnetic domains M, and the carbide particles Pb indicate carbide particles P on the domain wall W.

Since the carbide particles Pb impede the movement of the domain wall W, the domain wall W is in a state of being pinned by the carbide particles P.

Depending on the number of carbide particles P, all carbide particles P may be carbide particles Pa without carbide particles Pb. However, when the particle-to-particle distance of the carbide particles P is small compared to the size of the magnetic domains M, the carbide particles P are present near each magnetic domain M. In this case, even if the domain wall W moves, when it reaches the position of the carbide particle Pa, the movement of the domain wall W is blocked by the carbide particle Pa, so that the movement of the domain wall W stops. As a result, the domain wall W is in a state of being pinned by the carbide particles Pa present in the moving path.

Thus, when the carbide particles P are appropriately present in the crystal, the movement of the domain wall W is restricted.

In the high-temperature tempered structure of the stainless steel used for the probe 1, it is more preferable that more carbide particles P be formed at positions overlapping the domain wall W or near the domain wall W.

For example, the average value of the inter-particle distances of the carbide particles P in the high-temperature tempered structure is more preferably 0.5 μm or less. In this case, the high-temperature tempered structure becomes denser, and the carbide particles P are likely to be located at positions overlapping the domain wall W or near the domain wall W.

Here, the inter-particle distance of the carbide particles P is defined by the center-to-center distance of the carbide particles P. The inter-particle distance can be measured from images of the structure.

For example, the stainless steel used for the probe 1 more preferably includes 0.95 mass % or more and 1.2 mass % or less of carbon. In this case, the number of carbide particles P in the high-temperature tempered structure is appropriate. As a result, the high-temperature tempered structure becomes denser, and the carbide particles P are more likely to be located at positions overlapping the domain wall W or near the domain wall W.

When the number of carbide particles P in stainless steel increases, the corrosion resistance may decrease. In order to suppress deterioration of corrosion resistance, the stainless steel more preferably includes 16 mass % or more and 18 mass % or less of chromium.

An example of the method for producing the probe 1 will be described.

The probe 1 is manufactured by performing a first step, second step, and third step described below in this order.

In the first step, a substrate having the shape of the probe 1 is formed from a stainless steel material. For example, when the entire probe 1 is the substrate, the shape of the probe 1 is formed from a stainless steel material.

The stainless steel material more preferably includes carbon of 0.95 mass % or more and 1.2 mass % or less, and further preferably includes chromium of 16 mass % or more and 18 mass % or less.

For example, SUS440C may be used as the stainless steel material.

After the first step, the second step is performed.

In the second step, the substrate formed in the first step is quenched to turn it into martensite. For example, the substrate is held at a temperature of 1010° C. or higher and 1070° C. or lower and quenched at a cooling rate equal to or higher than the critical cooling rate.

After the second process, the third process is performed.

In the third step, the substrate is tempered so that a high-temperature tempered structure is formed from the martensite of the substrate quenched in the second step. For example, in order to make the high-temperature tempered structure mainly troostite, the substrate may be tempered at a temperature of 350° C. or higher and 450° C. or lower. In this case, the average value of the inter-particle distances of the carbide particles can be made 0.5 μm or less.

However, when sorbite is included in the high-temperature tempered structure, it may be tempered at a temperature exceeding 450° C. and 700° C. or less. In this case, the higher the temperature, the greater the proportion of sorbite.

Thus, the probe 1 made of stainless steel including a high-temperature tempered structure can be manufactured.

The operation of the ultrasonic treatment tool 100 according to this embodiment will be described.

The operator operates the input portion of the power supply unit 40 to set the output conditions of the ultrasonic treatment tool 100, for example, the set power for high-frequency energy output, the set power for ultrasonic energy output, and the like. The ultrasonic treatment tool 100 may be configured such that each value is individually set, or a set of set values is selected according to the surgical procedure.

The treatment portion 10 and the shaft 20 of the ultrasonic treatment tool 100 are inserted into the abdominal cavity through the abdominal wall, for example. The operator operates the movable handle 33 to open and close the treatment portion 10, and grips the biological tissue to be treated with the probe treatment portion 1a and the jaw 2.

The operator operates the output switch 35 after gripping the biological tissue with the treatment portion 10. When one of the two output switches 35 is pressed, the output switch 35 outputs a signal for application of a high-frequency voltage and driving of the ultrasonic transducer by the treatment portion 10. In this case, the control portion 41 of the power supply unit 40 transfers drive signals to the ultrasonic drive portion 42 and the high-frequency drive portion 43.

The high-frequency drive portion 43 applies a high-frequency voltage to the probe treatment portion 1a and the jaw 2 of the treatment portion 10 based on the control signal from the control portion 41, and causes a high-frequency current to flow through the biological tissue to be treated. When the high-frequency current flows, heat is generated in the biological tissue according to the electrical resistance of the biological tissue, and the temperature of the biological tissue rises. The temperature of the biological tissue at this time is, for example, about 100° C. As a result, proteins in the biological tissue are denatured, and the biological tissue is coagulated and sealed.

The ultrasonic drive portion 42 drives the ultrasonic transducer 52 based on the control signal from the control portion 41. As a result, the probe treatment portion 1a is ultrasonically vibrated in the longitudinal direction according to the driving frequency of the ultrasonic transducer 52. At this time, when the drive frequency approaches the natural frequency of the probe 1 and the probe 1 resonates, the ultrasonic vibration is amplified. In the resonance state, the energy of ultrasonic vibration is efficiently transmitted to biological tissue.

The temperature of the biological tissue rises due to frictional heat between the ultrasonically vibrating probe treatment portion 1a and the biological tissue. As a result, proteins in the biological tissue are denatured, and the biological tissue is coagulated and sealed.

The sealing effect of ultrasonic vibration on biological tissue is weaker than the sealing effect of high-frequency voltage application. Also, the temperature of the biological tissue is about 200° C., for example. As a result, the biological tissue collapses and the biological tissue is cut. In this manner, the biological tissue gripped by the treatment portion 10 is cut in a coagulated and sealed state.

In this way, treatment of the biological tissue by the ultrasonic treatment tool 100 is completed.

It is known that conventional stainless steel probes in ultrasonic treatment tools generate more heat during ultrasonic vibration than, for example, titanium alloy probes. When a conventional stainless steel probe undergoes some degree of continuous ultrasonic vibration, the Young's modulus decreases due to the temperature rise of the entire probe, changing the natural frequency of the probe. As a result, the resonance frequency also changes, so that the amplitude of the ultrasonic vibration becomes significantly smaller, which poses a problem in that the treatment cannot be continued.

The inventor of the present invention has conducted intensive research for the purpose of suppressing the heat generation of a stainless steel probe in an ultrasonic treatment tool to the extent that it does not interfere with the treatment, and found that heat generation can be suppressed by forming a probe using stainless steel including a high-temperature tempered structure, so as to arrive at the present invention.

The inventor of the present invention has paid attention to the energy loss presumed to be caused by domain wall movement induced by ultrasonic vibration as a heat-generating component of stainless steel, and has come up with the idea of distributing carbide particles in metal crystals.

First, the action of the probe of the comparative example using stainless steel in which carbide particles P do not exist will be described.

Figure 5:
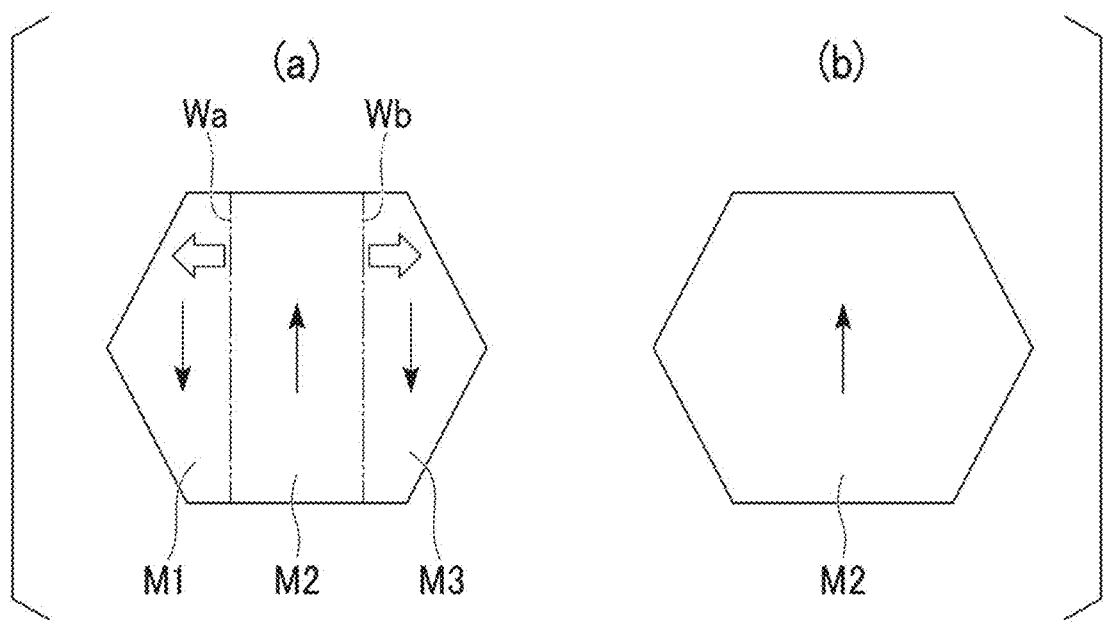
FIG. 5 is a schematic diagram showing an action of a probe for an ultrasonic treatment tool according to a comparative example.

FIG. 5 is a schematic diagram showing the action of the probe for an ultrasonic treatment tool according to the comparative example.

(a) in FIG. 5 schematically shows a metal crystal of a probe of a comparative example using stainless steel in which carbide particles P do not exist. It is supposed that magnetic domains M1, M2, and M3 are formed in the metal crystal of the probe of the comparative example.

When the probe of the comparative example is ultrasonically vibrated, the domain wall moves according to the stress generated by the ultrasonic vibration due to the magnetostriction reverse effect in the ferromagnetic material. For example, the domain wall Wa between the magnetic domains M1 and M2 and the domain wall Wb between the magnetic domains M2 and M3 move in directions indicated by white arrows. In this case, when the movement of the domain walls Wa and Wb is completed, the magnetic domains M1 and M3 disappear and only the magnetic domain M2 remains, as shown in (b) in FIG. 5.

As the magnetic domain walls Wa and Wb move and the direction of the magnetic moment changes, an eddy current loss occurs in the metal crystal or a magneto-mechanical hysteresis loss may occur. These energy losses are also called magnetic damping. Due to such magnetic internal friction, heat is generated in the probe of the comparative example.

Figure 6:
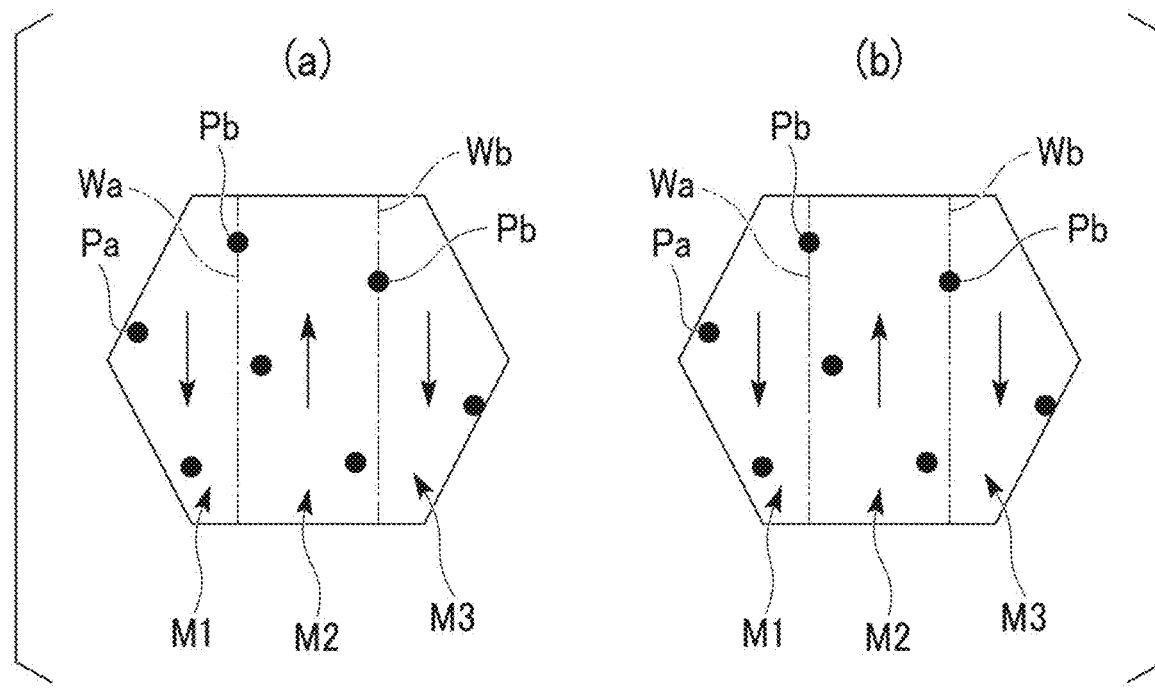
FIG. 6 is a schematic diagram showing an action of the probe for the ultrasonic treatment tool according to the embodiment of the present invention.

FIG. 6 is a schematic diagram showing the action of the probe for an ultrasonic treatment tool according to the embodiment of the present invention.

The metal crystal of the probe 1 of this embodiment shown in (a) in FIG. 6 is the same as the metal crystal of the probe of the comparative example, except that the carbide particles P are precipitated.

The carbide particles Pb located on the domain walls Wa and Wb have the function of inhibiting the movement of the domain walls Wa and Wb. As a result, even when the probe 1 is ultrasonically vibrated, the domain walls Wa. Wb do not move, and the magnetic domains M1, M2 and M3 do not change during the ultrasonic vibration as shown in (b) in FIG. 6.

As a result, no energy loss occurs due to the movement of the domain walls Wa, Wb, so heat generation due to the movement of the domain walls Wa, Wb is suppressed.

Thus, in the probe 1, when transmitting ultrasonic vibration, the heat generated due to the movement of the domain wall is suppressed, so the temperature rise is reduced. As a result, changes in the natural frequency of the probe 1 due to temperature rise are suppressed, so even if the drive frequency of the ultrasonic drive portion 42 is constant, ultrasonic vibration can be stably transmitted to the biological tissue.

According to the probe 1 of the present embodiment and the ultrasonic treatment tool 100 including the probe 1, since the structure of the stainless steel included in the probe 1 includes one or both of troostite and sorbite, heat generation in the stainless steel of the probe 1 can be suppressed. Therefore, treatment can be continued for a long time without, for example, controlling the temperature of the probe 1 or adjusting the drive frequency of the ultrasonic drive portion 42. For example, while a conventional stainless steel probe can only continue treatment for about 20 seconds, the probe 1 can continue treatment continuously for about 4 minutes.

Since the temperature change during ultrasonic vibration is suppressed, the probe 1 does not need to have a mechanism for adjusting the natural frequency. Therefore, with a simple configuration, it can be used for a long time without temperature control.

According to the method for producing a probe for an ultrasonic treatment tool according to the present embodiment, a structure including one or both of troostite and sorbite can be formed by heat-treating standard stainless steel. As a result, heat generation can be suppressed without using an expensive alloy including rare metal elements or the like, so that the production cost of the probe 1 can be reduced. Since the heat treatment of the probe 1 can be performed after forming the shape of the stainless steel into the shape of the probe 1, heat generation can be suppressed regardless of the shape of the probe.

Since the probe 1 according to this embodiment can be manufactured at low cost, it is suitable for single use and saves the trouble of sterilization.

As described above, according to the probe 1 and the ultrasonic treatment tool 100 including the probe 1, heat generation can be suppressed when stainless steel is included in the material of the probe, and it can be used for a long time without temperature control.

In addition, in the description of the above embodiment, the treatment portion 10 of the ultrasonic treatment tool has been described as an example of a forceps type in which the treatment is performed by sandwiching the biological tissue. However, the type of ultrasonic treatment tool is not limited to the forceps type. For example, the treatment portion of the ultrasonic treatment tool may be a saw type, spike type, meat tapping type, or the like, in which the treatment is performed by pressing the probe against the biological tissue without gripping the biological tissue between the treatment portions.

EXAMPLE

Next, Examples 1 to 4 relating to the embodiment will be described together with Comparative Examples 1 to 3.

The following Table 1 shows the composition of the stainless steel from which the probes of Examples 1-4 and Comparative Examples 1-3 were manufactured.

TABLE 1

| | COMPOSITION OF STAINLESS STEEL | | | | | | | ALLOY STANDARD |
|---|---|---|---|---|---|---|---|---|
| | C | Si | Mn | P | S | Ni | Cr | |
| EXAMPLE 1 | 0.98 | 0.27 | 0.31 | 0.02 | 0.002 | 0.15 | 16.9 | SUS440C |
| EXAMPLE 2 | 0.98 | 0.27 | 0.31 | 0.02 | 0.002 | 0.15 | 16.9 | SUS440C |
| EXAMPLE 3 | 0.98 | 0.27 | 0.31 | 0.02 | 0.002 | 0.15 | 16.9 | SUS440C |
| EXAMPLE 4 | 0.98 | 0.27 | 0.31 | 0.02 | 0.002 | 0.15 | 16.9 | SUS440C |
| COMPARATIVE EXAMPLE 1 | 0.04 | 0.5 | 1.5 | 0.02 | 0.015 | 9.2 | 19 | SUS304 |
| COMPARATIVE EXAMPLE 2 | 0.98 | 0.27 | 0.31 | 0.02 | 0.002 | 0.15 | 16.9 | SUS440C |
| COMPARATIVE EXAMPLE 3 | 0.98 | 0.27 | 0.31 | 0.02 | 0.002 | 0.15 | 16.9 | SUS440C |

The following Table 2 shows the heat treatment conditions and evaluation results of the probes of Examples 1 to 4 and Comparative Examples 1 to 3.

0.31 mass %, phosphorus (P) of 0.02 mass %, sulfur (S) of 0.002 mass %, nickel (Ni) of 0.15 mass %, and chromium (Cr) of 16.9 mass %.

The material was formed into the shape of the probe 1 as shown in FIG. 3 by lathe processing (first step).

After that, the part formed in the shape of the probe 1 was quenched based on the heat treatment conditions shown in Table 1 (second step).

In the second step, the part was held in a heat treatment furnace at a quenching temperature of 1040° C. for 10 minutes. After this, the part was oil-cooled at a cooling rate above the critical cooling rate. This completes the hardening of the part.

After that, the quenched part was tempered under the heat treatment conditions shown in Table 1 (third step).

In the third step, the part was held in a heat treatment furnace at a tempering temperature of 400° C. for 1 hour. After this, the part was oil-cooled to room temperature. This completes the tempering of the part.

Thus, the probe 1 of Example 1 was manufactured.

Examples 2 to 4

As shown in Table 1, the stainless steel material from which the probes 1 of Examples 2 to 4 were manufactured was the same as the material of Example 1.

The production method of the probe 1 of Examples 2 to 4 was the same as that of Example 1, except that the tempering temperature was different, as shown in Table 2.

In the third step in Example 2, the tempering temperature was 350° C.

In the third step in Example 3, the tempering temperature was 450° C.

In the third step in Example 4, the tempering temperature was 500° C.

TABLE 2

| | HEAT TREATMENT CONDITION | | | EVALUATION RESULT | | |
|---|---|---|---|---|---|---|
| | QUENCHING TEMPERATURE (° C.) | TEMPERING TEMPERATURE (° C.) | MAIN STRUCTURE | AVERAGE INTER-PARTICLE DISTANCE OF CARBIDE PARTICLES (μm) | TEMPERATURE RISE (deg) | EVALUATION |
| EXAMPLE 1 | 1040 | 400 | TROOSTITE | 0.4 | 45 | A |
| EXAMPLE 2 | 1040 | 350 | TROOSTITE | 0.3 | 30 | A |
| EXAMPLE 3 | 1040 | 450 | TROOSTITE | 0.5 | 60 | A |
| EXAMPLE 4 | 1040 | 500 | SORBITE | 0.7 | 80 | B |
| COMPARATIVE EXAMPLE 1 | 1040 | 400 | AUSTENITE | — | 300 | C |
| COMPARATIVE EXAMPLE 2 | 1040 | 300 | BAINITE | — | 175 | C |
| COMPARATIVE EXAMPLE 3 | 1040 | — | MARTENSITE | — | 200 | C |

Example 1

As shown in Table 1, SUS440C was used as the stainless steel material for producing the probe 1 of Example 1. The shape of the raw material was a round bar with a diameter of 8 mm.

The composition of the material was carbon (C) of 0.98 mass %, silicon (Si) of 0.27 mass %, manganese (Mn) of Comparative Example 1

As shown in Table 1, SUS304 was used as the stainless steel material for producing the probe of Comparative Example 1. The shape of the raw material was a round bar with a diameter of 8 mm.

The composition of the material was carbon (C) of 0.04 mass %, silicon (Si) of 0.5 mass %, manganese (Mn) of 1.5 mass %, phosphorus (P) of 0.02 mass %, sulfur (S) of 0.015 mass %, nickel (Ni) of 9.2 mass %, and chromium (Cr) of 19 mass %.

The production method of Comparative Example 1 was the same as that of Example 1, except that the raw materials were different, as shown in Table 2.

Comparative Example 2

As shown in Table 1 and Table 2, the probe of Comparative Example 2 was manufactured in the same manner as in Example 1, except that the tempering temperature was set to 300° C.

Comparative Example 3

As shown in Table 1 and Table 2, the probe of Comparative Example 3 was manufactured in the same manner as in Example 1, except that tempering was not performed.
[Evaluation]

Using the manufactured probes of each example and each comparative example, the determination of the structure, the measurement of the inter-particle distance of the carbide particles, and the measurement of the temperature rise of the probe were performed.
[Determination of Organization]

For the determination of the structure, it was determined whether or not austenite was included by X-ray diffraction measurement (XRD), and if austenite was not included, microscopic observation was performed.

Samples for X-ray diffraction measurement were prepared from the probes of each example and each comparative example.

For each sample cross section, profile measurement was performed using an X-ray diffractometer Smartlab (which is a trade name and is manufactured by Rigaku Corporation). Cu (20 kV) was used as a tube, and an XRD profile (2θ scan) in the range of 30° to 110° was obtained under the conditions of a scan step of 0.03° and a scan speed of 20°/min.

According to this measurement, when austenite was included, there was a peak near 43° in addition to the peak near 44.5°. When neither peak appeared, it was found that austenite was not included.

Figure 7:
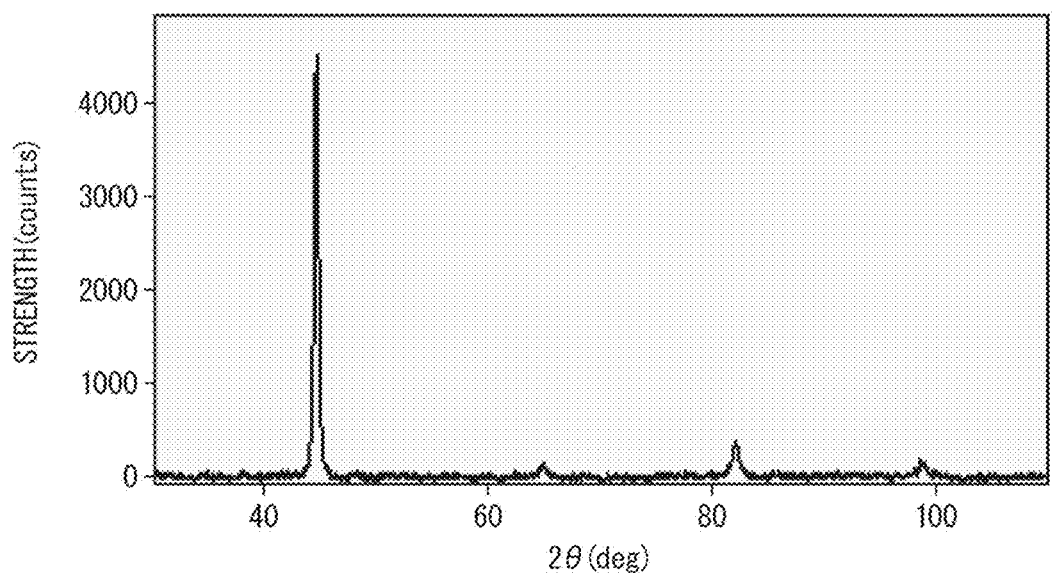
FIG. 7 is a graph showing an example of an XRD profile when austenite is not included.

FIG. 7 is a graph showing an example of an XRD profile when austenite was not included. The horizontal axis of the graph is 2θ (deg), and the vertical axis is intensity (counts).

The graph shown in FIG. 7 is the XRD profile of Example 4. The probe 1 of Example 4 did not include austenite, since no peak appeared near 43°.

Next, the microscopic observation will be described.

Samples for microscopic observation were prepared from the probes of each example and each comparative example.

Each sample was polished with a cross section-polishing machine after being embedded in epoxy resin. After rough polishing with waterproof abrasive paper (up to #1500), the sample surface was mirror-finished using diamond slurry (up to 0.25 μm) to prepare a sample for observation.

The structure observation method by which the presence or absence of martensite was determined will be described.

In the structure observation method 1, the observation sample was immersed in a corrosive solution (copper sulfate of 5 g, hydrochloric acid of 100 mL, ethanol of 100 mL, and water of 100 mL) to be corroded.

A photograph of the structure of the corroded observation sample was taken using a digital microscope DSX510 (which is a trade name and is manufactured by Olympus Corporation). The photographing was performed under the condition that the magnification of the objective lens was 40 times and the zoom magnification was 6 times.

In the obtained structure photograph (grayscale), an 80-μm square measurement area was observed to determine whether martensite was included in the measurement area.

When martensite was included, a dark black structure was observed. A gray structure was observed when martensite was not included.

The structure observation method II by which the structure was determined when martensite was not included will be described.

Figure 8:
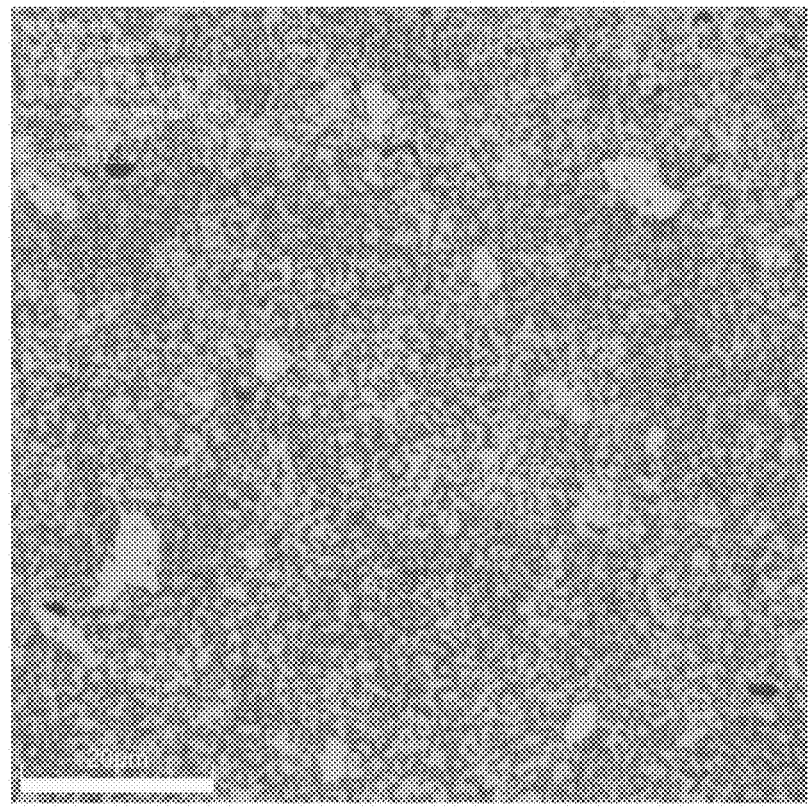
FIG. 8 is a photograph showing an observation example of a structure composed of ferrite and cementite.
Figure 9:
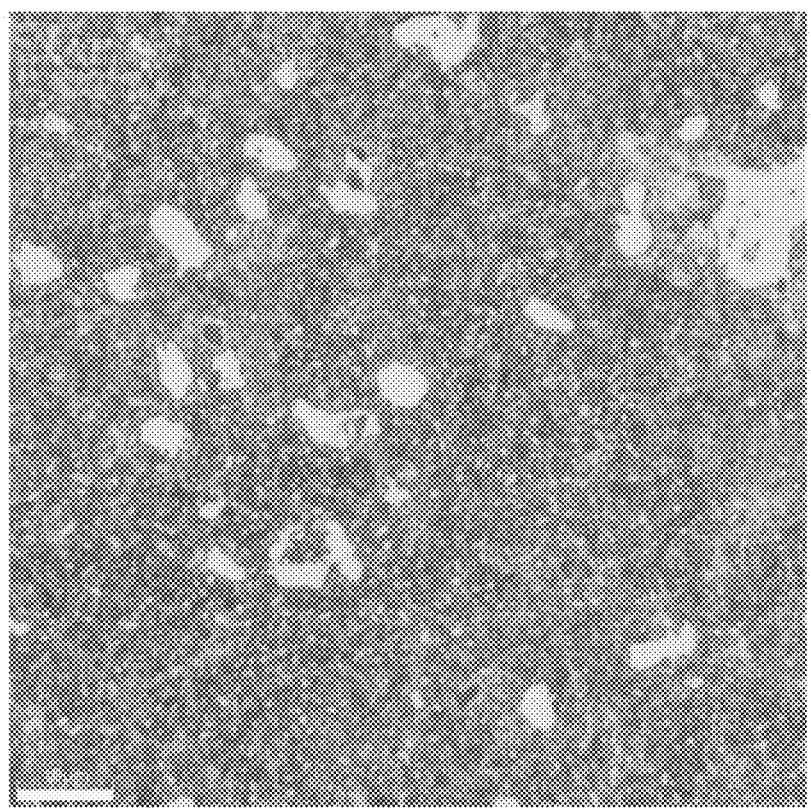
FIG. 9 is a photograph showing an observation example of a structure including troostite and sorbite.
Figure 10:
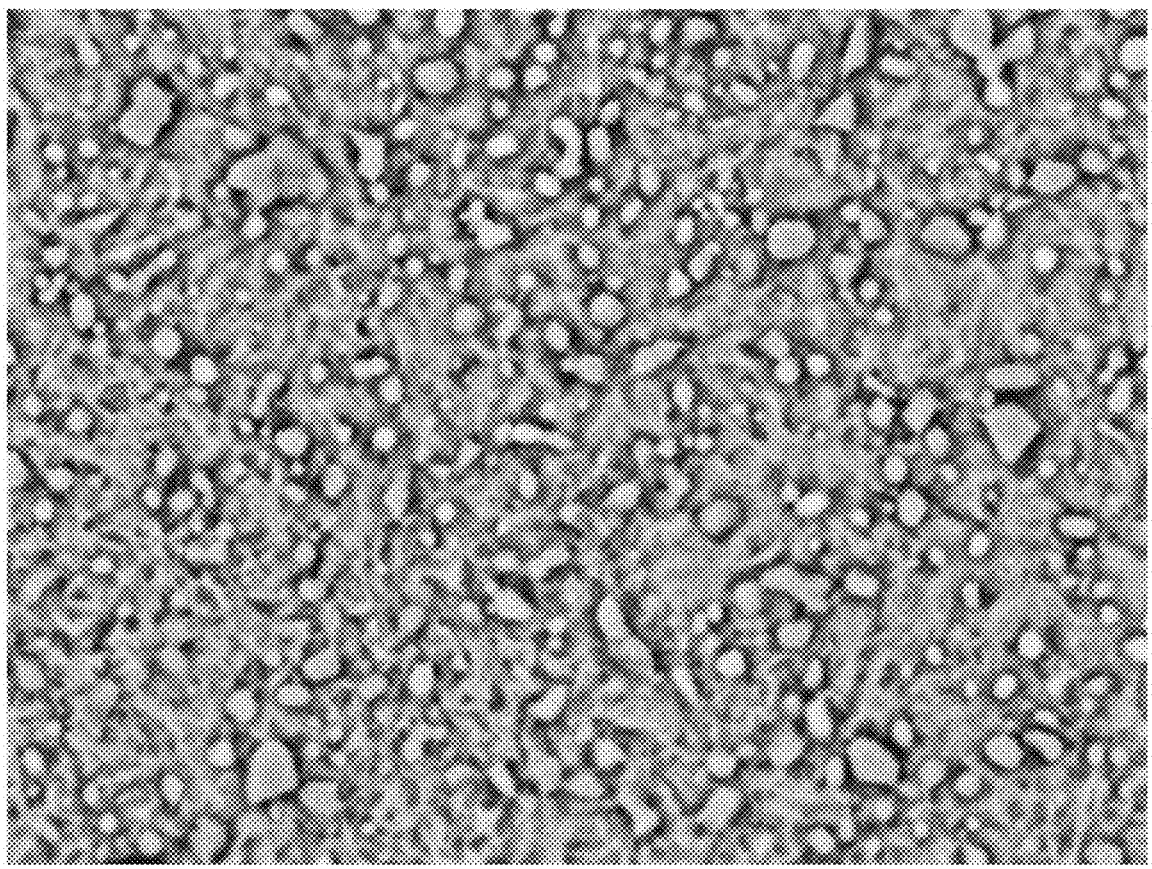
FIG. 10 is a photograph by a scanning electron microscope showing an observation example of sorbite.

FIG. 8 is a photograph showing an observation example of a structure composed of ferrite and cementite. FIG. 9 is a photograph showing an observation example of a structure including troostite and sorbite. FIG. 10 is a scanning electron microscope photograph showing an observation example of sorbite.

The sample for observation was photographed in the same manner as in structure observation method I, except that the etchant was changed to aqua regia. However, in structure observation method II, full-color structure photographs were taken.

Observing the measurement area of 80 μm square in the obtained structure photograph (full color), ferrite+cementite and troostite (sorbite) were discriminated.

In the case of ferrite+cementite, the carbide was layered or particulate, but even if it was particulate, the particle size exceeded 1 μm. On the other hand, troostite (sorbite) is a particulate carbide and has a particle size of 1 μm or less.

In the case of ferrite+cementite, for example, a photograph as shown in FIG. 7 was taken. In the case of a full-color photograph, in the observation example of FIG. 7, many black-rimmed circles (spherical cementite) were observed on a white substrate (ferrite), and the particle size was large, so it was distinguished from troostite and sorbite.

In the case of troostite (sorbite), for example, a photograph as shown in FIG. 8 was taken. In the case of full-color photographs, a brownish matrix (troostite/sorbite) and white particles (carbides) were observed, which were distinguished from the ferrite+cementite structure due to the small particle size of the carbide particles.

Troostite and sorbite were distinguished by observation with a scanning electron microscope (SEM) after corrosion with aqua regia. For example, the structure shown in FIG. 10 was sorbite because the carbide particles existed independently of the ferrite.

As for bainite, no particular photograph is shown, but since the particle shape is needle-like, it could be distinguished from ferrite+cementite and troostite (sorbite) by microscopic observation.
[Measurement of Distance Between Carbide Particles]

When the carbide particles could be identified by the structure observation method II, the inter-particle distance defined by the center-to-center distance of the carbide particles was measured. An average value was calculated from 30 inter-particle distances in the measurement area of the 10 μm square SEM image, and described in the "average inter-particle distance of carbide particles" column of Table 2.
[Measurement of Probe Temperature Rise]

The ultrasonic driving unit 42 was connected to the probes of each example and each comparative example, and the probes were ultrasonically vibrated for 5 minutes. The driving conditions by the ultrasonic driving unit 42 were an amplitude of 30 μm and a driving frequency of 47 kHz. A radiation thermometer was used to measure the temperature of the probe before and immediately after the ultrasonic vibration was started, and the temperature rise caused by the ultrasonic vibration was measured.

[Evaluation Results]

According to the determination of the structure described above, as shown in Table 2, the structures of Examples 1 to 3 were mainly troostite. The structure of Example 4 was primarily sorbite.

The structures of Comparative Examples 1, 2, and 3 were austenite, bainite, and martensite, respectively.

As shown in Table 2, the average values of the inter-particle distances in Examples 1 to 4 were 0.4 µm, 0.3 µm, 0.5 µm and 0.7 µm, respectively.

The average value of the distance between particles in Examples 1 to 5, in which the structure was mainly troostite, was 0.5 µm or less. The average inter-particle distance in Example 4, in which the structure was primarily sorbite, exceeded 0.5 µm.

No carbide particles precipitated in Comparative Examples 1 to 3.

As shown in Table 2, the temperature rises in Examples 1 to 4 were 45 deg, 30 deg, 60 deg, and 80 deg, respectively.

The temperature rises in Comparative Examples 1 to 3 were 300 deg, 175 deg, and 200 deg, respectively.

Each example and each comparative example were evaluated based on the measured temperature rise. If the temperature rise was 0 deg or more and 75 deg or less, it was defined as "very good" (described as "A" in Table 2), and if it was over 75 deg and 150 deg or less, it was defined as "good" (described as "B" in Table 2), and if it exceeded 150 deg, it was defined as "not good" (described as "C" in Table 2).

As shown in Table 2, the probes 1 of Examples 1 to 3 were judged to be "very good". The probe 1 of Example 4 was judged to be "good".

On the other hand, Comparative Examples 1 to 3 were all judged as "not good".

The reason the temperature rise in Example 4 was larger than that in Examples 1 to 3 is that the structure was mainly sorbite, and as a result, the average value of the distance between particles of carbide particles was as large as 0.7 µm. It is believed that the large interparticle distance of the carbide particles reduced the number of domain walls whose movement was inhibited by the carbide particles.

In the case of Comparative Examples 1 to 3, the temperature rise was larger than that of Examples 1 to 4 because there was no precipitation of carbide particles that inhibit the movement of the domain wall.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

INDUSTRIAL APPLICABILITY

According to the above-described embodiments, it is possible to provide an ultrasonic treatment tool, a method of producing a probe for an ultrasonic treatment tool, and an ultrasonic treatment tool, in which when stainless steel is included in the material of the probe, heat generation can be suppressed and the probe can be used for a long time without temperature control.

What is claimed is:

1. A probe for an ultrasonic treatment tool, the probe being configured to transmit ultrasonic vibration to a biological tissue, the probe comprising:
   a substrate including a stainless steel, a structure of the stainless steel including one or both of troostite and sorbite.

2. The probe according to claim 1, wherein an average inter-particle distance among carbide particles in one or both of the troostite and the sorbite is 0.5 µm or less.

3. The probe according to claim 1, wherein the stainless steel includes carbon of 0.95 mass % or more and 1.2 mass % or less.

4. The probe according to claim 3, wherein the stainless steel includes chromium of 16 mass % or more and 18 mass % or less.

5. A method for producing a probe for an ultrasonic treatment tool, the method comprising:
   a first step of forming a substrate having a shape of the probe from a stainless steel material;
   a second step of holding the substrate at a temperature of 1010° C. or higher and 1070° C. or lower and quenching at a cooling rate equal to or higher than a critical cooling rate; and
   a third step of tempering the substrate at a temperature of 350° C. or higher and 700° C. or lower.

6. The method according to claim 5, wherein, in the third step, the substrate is tempered at a temperature of 350° C. or higher and 450° C. or lower.

7. An ultrasonic treatment tool comprising the probe according to claim 1.

* * * * *